Nov. 30, 1976
S. D. McGREDY
ROSE PLANT
Filed Oct. 6, 1975
Plant Pat. 3,985
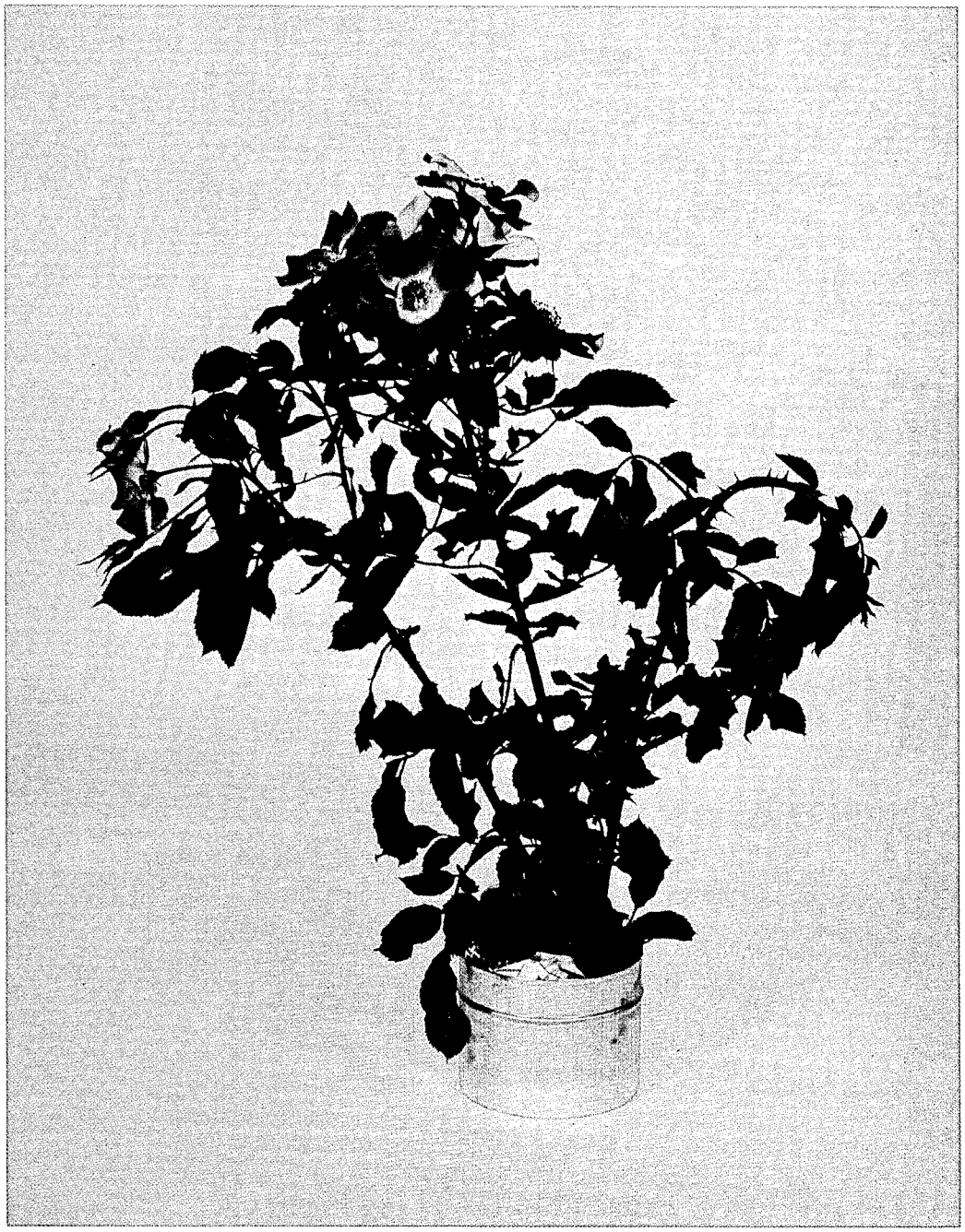

United States Patent

Plant Pat. 3,985

Patented Nov. 30, 1976

3,985

ROSE PLANT

Samuel D. McGredy, P.O. Box 14-100,
Auckland, New Zealand

Filed Oct. 6, 1975, Ser. No. 620,201

Int. Cl.[2] A01H 5/00

U.S. Cl. Plt.—1 1 Claim

The present invention relates to a new and distinct variety of rose plant of the shrub class, which was originated by my crossing as seed parent a rose seedling of a cross of "Little Darling" × "Goldilocks" with as pollen parent a seedling of "Evelyn Fison × [R. 'Coryana' × Tantau's Triumph) × "Picasso"].

Among the novel characteristics possessed by this new variety which distinguish it from its parents and all other varieties of which I am aware are: (1) almost continuous blooming habit, (2) brilliant scarlet single blooms in substantial clusters with individual blooms displaying a distinct white "eye," and (3) excellent hardiness and virtual immunity to diseases, e.g., blackspot, mildew and rust. Asexual reproduction by budding of the new variety as performed in Clackamas County, Oreg., shows that the foregoing and other distinguishing characteristics come true to form and are established and transmitted through succeeding propagations.

The accompanying drawing shows typical specimens of the vegetative growth and flowers of the new variety as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "45B" is plate 45B of the Royal Horticultural Society Color Chart.

Parentage: Seedling.

*Seed parent.*—"Little Darling" × "Goldilocks."

*Pollen parent.*—"Evelyn Fison" × [R. 'Coryana' × Tantau's Triumph) × "Picasso"].

Class: Shrub.

The following observations are made of specimens grown outdoors at Clackamas County, Oreg., during the month of July.

1. FLOWER

Blooming habit: Continuous, earlier than average. Profuse display repeating blooms before first crop is gone.

A. Bud:

(*1*) *Size.*—Very small, usualy ⅝" to ¾".

(*2*) *Form.*—Long pointed buds.

(*3*) *Color.*—When sepals first divide: 46A. When petals begin to unfurl: 45B. When half-blown: inside of petals—46B; reverse side of petals—55C.

(*4*) *Sepals.*—Long narrow acuminate glabrous with hirsute edges—143A.

(*5*) *Peduncle.*—Length—1" to 1½"; Aspect—Radiate. Strength—Wiry. Color—144C.

B. Bloom:

(*1*) *Sizes.*—Average size when fully expanded—2½ to 3 inches.

(*2*) *Borne.*—Sprays.

(*3*) *Form.*—Flat, single, ruffled.

(*4*) *Petalage.*—Number of petals under normal conditions—5 (with 2 to 3 petaloids).

(*5*) *Colors.*—Outer petals—45B. Base of petals (point of attachment)—27D about ⅜". Reverse of petals—49D with occasional darker markings 52B. General tonality from a distance—red with white colored "eye" surrounding fluffy golden stamens.

(*6*) *Color change.*—As bloom ages—slight 46B. General tonality—Red with distinct white "eye" becoming more evident since stamens recurve. After three or more days—same.

C. Petals:

(*1*) *Texture.*—Thick and stiff.

(*2*) *Appearance.*—Satiny.

(*3*) *Form.*—Rounded triangular, often acuminate.

(*4*) *Arrangement.*—Regular.

(*5*) *Petaloids in center.*—Few, 1 to 3.

(*6*) *Persistence.*—Drop clean.

(*7*) *Fragrance.*—Faint—tea.

(*8*) *Lasting quality.*—Very long lasting on plant and cut.

2. REPRODUCTIVE ORGANS

A. Stamens filaments and anthers:

(*1*) *Arrangement.*—Regular but of varying lengths.

(*2*) *Color.*—15A anthers edged 26B.

B. Pollen: Color: 17A.

C. Styles: Short, few, 20–30 glandular.

D. Stigmas: Color—10B.

E. Hips: Shape: Small, ovoid. Size: ½" to ¾". Color: 33B when mature. Do seeds protrude? So few—2 to 5 that they are completely encased.

3. PLANT

A. Form: Spreading, dense, globose, shrubby.

B. Growth: Vigorous, densly branching. Height attained—4½ to 5 ft.

C. Foliage: Compound—5 to mostly 7 leaflets.

(*1*) *Size.*—Small 2½" to 3" long x 1" to 1½" wide.

(*2*) *Quantity.*—Abundant and dense.

(*3*) *Color.*—New foliage: Upper side—187A; under side—153D with overcast 185C. Old foliage: Upper side—147A; under side—147B.

(*4*) *Shape.*—Long oval pointed serrate.

(*5*) *Texture.*—Upper side—Flat, leathery; under side—flat stippled.

(*6*) *Edge.*—Serrate.

(*7*) *Serration.*—Sharp with points curving forward.

(*8*) *Leaf stem.*—Color—146C; under side—146D.

(*9*) *Stipules.*—Medium length with short, narrow appendages lightly fimbriate.

(*10*) *Resistance to disease.*—Blackspot—excellent. Mildew—excellent. Rust—excellent.

D. Wood:

(*1*) *New wood.*—Color—146D with purple tints; bark—smooth with waxy blook.

(*2*) *Old wood.*—Color—146C; bark—smooth.

E. Thorns:

(*1*) *Thorns.*—Quantity: On main stalks from base-ordinary, uniform on laterals from stalk—few, smaller. Form—long pointed slightly recurved. Length—medium—about ½". Color (when young)—146D at tips, 185C at base. Position—regular, evenly distributed.

(*2*) *Prickles.*—Quantity: On main stalks—fewer than average—uniform distribution; on lateral—few, scattered.

F. Winter hardiness: Completely hardy even in northern Midwest.

I claim:

1. A new and distinct variety of rose plant of the shrub class, substantially as shown and described, characterized particularly by brilliant scarlet single blooms with individual ones displaying a distinct white eye, a plant of almost continuous blooming habit and excellent hardiness and resistance to disease.

No references cited.

ROBERT E. BAGWILL, Primary Examiner